United States Patent [19]

Beevers

[11] Patent Number: 4,802,474
[45] Date of Patent: Feb. 7, 1989

[54] PROTECTIVE COVER FOR TRACHEOTOMY TUBE

[76] Inventor: Katherine K. Beevers, 11075 Montana Ave., Boise, Id. 83704

[21] Appl. No.: 93,311
[22] Filed: Sep. 4, 1987
[51] Int. Cl.⁴ ............................................. A01M 16/00
[52] U.S. Cl. ............................ 128/200.26; 128/207.14
[58] Field of Search ......... 128/200.26, 207.14–207.17, 128/132 R; 623/9

[56] References Cited

U.S. PATENT DOCUMENTS

| | | | |
|---|---|---|---|
| 1,065,920 | 7/1913 | Crowe | 128/207.14 |
| 2,039,142 | 4/1936 | Brehm | 128/207.17 |
| 2,393,326 | 1/1946 | Lane | 128/207.14 |
| 2,491,647 | 12/1949 | Colavita | 128/207.17 |
| 3,066,674 | 12/1962 | Capra | 128/207.16 |
| 3,137,299 | 6/1964 | Tabor | 128/207.16 |
| 3,330,271 | 7/1967 | Hozier | 128/207.14 |
| 3,952,335 | 4/1976 | Sorce et al. | 128/207.16 |
| 4,325,366 | 4/1982 | Tabor | 128/207.16 |
| 4,582,058 | 4/1986 | Depel et al. | 128/207.16 |

FOREIGN PATENT DOCUMENTS 0078685  5/1983  European Pat. Off. ............... 623/9

Primary Examiner—Edward M. Coven
Assistant Examiner—K. M. Reichle
Attorney, Agent, or Firm—Frank J. Dykas

[57] ABSTRACT

Device for selectively preventing ingestion of foreign objects through a tracheal opening. One piece design particularly adaptable to inexpensive production from resilient material and easy maintenance.

2 Claims, 2 Drawing Sheets

PROTECTIVE COVER FOR TRACHEOTOMY TUBE

BACKGROUND OF THE INVENTION

1. Field of Invention

This invention relates to tracheotomy devices and more particularly to protective covers for tracheotomy tubes.

2. Description of the Prior Art

The prior art discloses a variety of tracheal appliances to be used following surgery and opening of an air passage or breathing hole in a patient's neck. One branch of this art is concerned with providing means to keep this airway open. Typical of this art is MONTGOMERY, U.S. Pat. No. 4,269,184, which discloses a tracheal cannula insertable into a patient's neck by surgical procedures which comprises an outer flange and an inner flange and barbs assigned to engage the tissue surrounding the opening. COHN, U.S. Pat. No. 2,786,469, discloses a similar device with the added feature of a removable plug to permit the wearer to close the air breathing hole at will. When the plug is installed, the air passageway is closed, requiring the wearer to breathe through his mouth or nose. Another branch of this art discloses devices for preventing expulsion of mucus and other materials through the airway. Typical of this art are LICHTENBERGER, U.S. Pat. No. 4,598,705, which shows a disposable receptacle, and COLAVITA, U.S. Pat. No. 2,491,647, which discloses a dismountable canister which utilizes a bayonet lock to hold it in place.

Another branch of this art is exemplified by HOZIER, U.S. Pat. No. 3,330,271, which discloses devices for preventing the aspiration of foreign objects into the lungs through the tracheal opening. HOZIER discloses a stoma button with removable mesh filter comprising three separate, interlocking pieces in the preferred embodiment.

There are two general catagories of problems associated with tracheal tubes. The first is when the tracheal tube is plugged because the tracheal tube appliance, or stoma button, collapses or is crushed. Collapse is likely to occur if the patient falls or is involved in an automobile collision or some other similar type of trauma. The devices disclosed in LICHTENBERGER and COLAVITA are readily subject to this type of damage.

The second dangerous condition is the occlusion of the tracheal airway either because the tracheal tube opening is blocked or because some foreign matter, such as a gauze pad, has been aspirated. Some of the common methods by which occlusion of the tracheal tube is inadvertently accomplished include: clothing being sucked into the tracheal tube; a filter becoming plugged by dust or dirt resulting from either a wind storm or the patient falling; a patient, who has a fat chin who falls asleep, with the head and chin falling forward to cover the tracheal tube opening; or a jerry rigged gauze filter being sucked into the tracheal tube.

Regardless of how it happens, whether the reason is that the tube is crushed, or occluded, there is an immediate need, in all of the prior art cases to remove the cover, filter or stoma button, before the patient can be suctioned or positively ventilated.

There is another problem with current tracheal covers which, in rare instances, does cause significant problem. That is that most of the products on the market, when made from plastic materials are radio wave transparent and hence, not visible on a developed X-ray. If for some reason the tracheal cover is shattered or broken and part of it is aspirated by the wearer, and it is radio wave transparent, then the only method of finding it in the bronchial tubes is by surgical exploration.

Accordingly, it is an object of this invention to provide a tracheal tube protective cover manufactured of resilient material and of such design that it will not occlude the air passageway in the event the protective cover is accidentally crushed. It is another object of this invention to provide a protective cover which does not have to be removed in order to suction the wearer or, as the case may be, to positively ventilate said wearer.

A third object is to provide a protective cover which can be easily and quickly removed regardless of lighting conditions and whether or not the cover is covered with blood, mucus or other body fluids. A fourth object is to provide a protective cover which, by its design, prevents occlusion by clothing, and even if exposed, will provide a pleasing appearance so as to minimize the wearer's embarrassment. A fifth object is to provide a protective cover which is radio wave opaque in the event it, or any portion thereof, is aspirated by the wearer. And finally, it is an object of this invention to provide a protective cover which is inexpensive to manufacture.

SUMMARY OF THE INVENTION

These objects are accomplished by a collar made of a resilient plastic material which is radio wave opaque, and adapted in size and shape to frictionally engage the outside of the end of the tracheal tube next adjacent the skin surface. In the first preferred embodiment a ventilation flange, extending radially outward from the collar provides a hand hold for installation and removal of the protective cover from the tracheal tube. An end plate, held in spaced relationship to the ventilation flange by cage bars, is provided to protect the tracheal opening from occlusion and to prevent the ingestion of foreign objects of selected size. The cage bars are spaced far enough apart to allow insertion between the cage bars of an suction catheter (aspirating tubular device) of standardized size. Additionally, the ventilation flange is sized to permit the use of standardized ventilation devices such as an AMBO or pressure ventilator with a standard 22 mm adapter. Additionally, the distance separating the end plate from the ventilation flange is such that, even if the protective cover were to be crushed, the end plate would be laterally displaced and, would not occlude the tracheal opening.

In a second preferred embodiment the collar is also adapted in size and shape to frictionally engage the outside of the end of the tracheal tube. A circumferential ridge or barb integral with said collar is provided at the insertion end to pass through the stoma to inhibit the removal of the collar once installed. In this embodiment the ventilation flange is expanded to provide a cosmetic cover over the neck area adjoining the stoma.

DETAILED DESCRIPTION OF THE PREFERRED EMBODIMENTS

Figure 1:
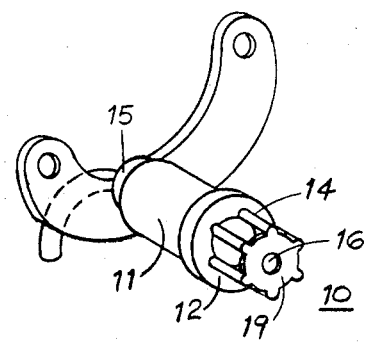
FIG. 1 is a schematic representational view of the preferred embodiment attached to a tracheal tube.
Figure 2:
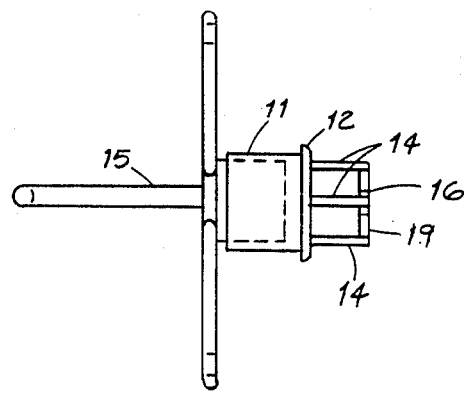
FIG. 2 is a top plan view of the preferred embodiment attached to a tracheal tube.
Figure 3:
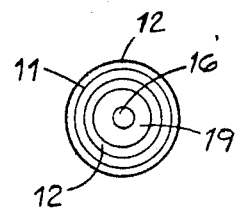
FIG. 3 is a bottom view of the preferred embodiment.
Figure 4:
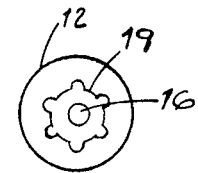
FIG. 4 is a top view of the preferred embodiment.

In the preferred embodiment of this protective cover 10, a collar 11 is adapted in size and shape to frictionally engage the outside end of a tracheal tube 15, as is shown in FIGS. 1 and 2. Collar 11 is fabricated integrally with vent flange 12. Foreign objects of a selected size are kept out of the airway created by tracheal tube 15, by means of a cage which is integral with the rest of the device. Circular end plate 19 is mounted in spaced relationship with the vent flange 12, and interconnected therewith by a plurality of cage bars 14. The spacing of cage bars 14, one from another, and the distance between vent flange 12 and end plate 19 determines the size of foreign objects which will be kept out of the airway by this protective cover 10. The space between the cage bars is also sized so as to permit the introduction of a standardized aspirating tube. This eliminates the need to remove the cover in the event that aspiration is required.

Additionally, protective cover 10 is made of a resilient medical grade plastic so that in the event the protective cover were to be crushed by impact with a hard object, end plate 19 will be laterally displaced and will not cause an occlusion of the tracheal opening. Hopefully, if the impact is not too severe, the resilient characteristics of the medical grade plastic will cause the end plate to return to its normal configuration. The medical grade resilient plastic also contains chemicals which make it radio wave opaque, and thus clearly visible on developed X-rays in the event it, or any portion thereof, is aspirated by the wearer. Also, hole 16 is provided in end plate 19 to further minimize the possibility of an occlusion occurring by reason of collapse or crushing of the protective cover.

In this embodiment, protective cover 10, is not embedded into the neck of the user, but rather is frictionally mounted to a conventional tracheal tube. Vent flange 12, as previously stated, is fabricated integrally with collar 11, and extends radially outward therefrom to provide a convenient finger hold for removal of protective cover 10 irregardless of whether the surface conditions are slippery by reason of being covered with body fluids, blood, mucus, or whatever. It is an important safety feature in that it requires no special skills or knowledge to release protective cover 10 and as a result could be performed by anyone, including a small child, in the event of an emergency. In this embodiment, the invention can be more readily removed for cleaning or replacement.

Figure 5:
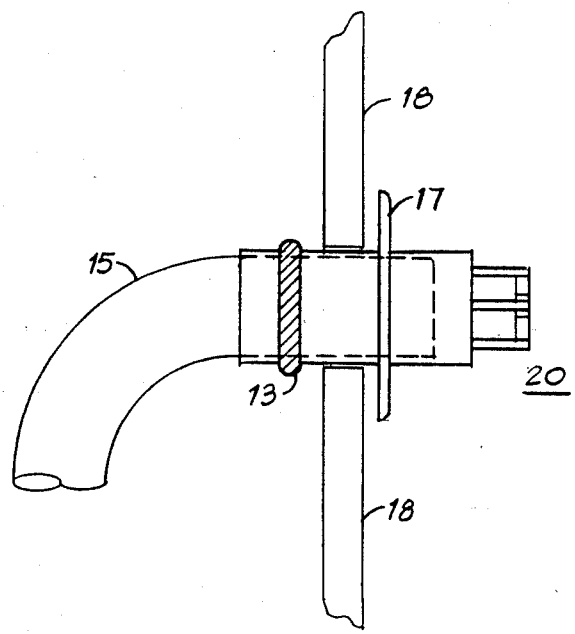
FIG. 5 is an expanded, representational, side view of a second preferred embodiment.

In a second embodiment, 20, as is shown in FIG. 5, what serves as vent flange 12 in the first preferred embodiment, is expanded radially outward to form a surface flange 17 which covers the annular space between the tracheal tube 15 and the surrounding skin surface 18, and thereby conceals the edge of the incision. Also incorporated into this second embodiment is ridge ring 13 which is circumferential and engages the surrounding skin tissue 18 of the stoma when fully inserted, thereby preventing accidental dislodgment of the device 20.

Being an integral construction of resilient material, protective covers 10 and 20 are particularly well adapted to mass production and inexpensive fabrication techniques. Further, it is more aesthetically pleasing than that shown or disclosed in the prior art.

While there is shown and described the present preferred embodiments of the invention, it is to be distinctly understood that the invention is not limited thereto but may be variously embodied to practice within the scope of the following claims.

Accordingly, what I claim is:

1. A protective cover for a tracheotomy tube comprising:
   a collar adapted in size and shape to fit over and frictionally engage the end of the tracheotomy tube;
   an end plate in spaced relation with said collar;
   a plurality of cage bars interconnecting said end plate and collar, said plurality of cage bars aligned in parallel cylindrical spaced relationship, and further, spaced at sufficient intervals to permit the insertion of a standardized aspirating tube between any two cage bars;
   a surface flange integral with said frictional engagement means and said inhalation prevention means, adapted in size and shape to cover the annular space between said frictional engagement means and the surrounding tissue of the wearer's neck.

2. The protective cover of claim 1 wherein said protective cover is made from a radio opaque medical grade plastic.

* * * * *